United States Patent
Ropo et al.

(10) Patent No.: US 12,138,477 B2
(45) Date of Patent: Nov. 12, 2024

(54) METHOD AND APPARATUS TO DETECT AND RESPOND TO RADIATION TREATMENT PLAN SPOT WEIGHT EDITS

(71) Applicant: Siemens Healthineers International AG, Steinhausen (CH)

(72) Inventors: Matti Ropo, Helsinki (FI); Petri Hirvonen, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 420 days.

(21) Appl. No.: 17/555,741

(22) Filed: Dec. 20, 2021

(65) Prior Publication Data
US 2023/0191149 A1    Jun. 22, 2023

(51) Int. Cl.
*A61N 5/10*    (2006.01)

(52) U.S. Cl.
CPC ......... *A61N 5/1031* (2013.01); *A61N 5/1048* (2013.01); *A61N 2005/1087* (2013.01)

(58) Field of Classification Search
CPC ............. A61N 5/1031; A61N 5/1048; A61N 2005/1087
See application file for complete search history.

(56) References Cited

U.S. PATENT DOCUMENTS

2012/0136677 A1* 5/2012 Ziegenhein ............ G16H 20/40
                                                                    705/2
2016/0236008 A1    8/2016 Otto

FOREIGN PATENT DOCUMENTS

EP          2994195 A2    3/2016

OTHER PUBLICATIONS

Ma, Jiasen et al.; "A GPU-accelerated and Monte Carlo-based intensity modulated proton therapy optimization system", Medical Physics, AIP, Melville, NY, US, vol. 41, No. 12, Nov. 18, 2014 (Nov. 18, 2014), KP012192008, ISSN: 0094-2405, DOI: 10.1118/1.4901522 [retrieved on Jan. 1, 1901].
Extended European Search Report from European Application No. 22214137.6 dated May 12, 2023; 7 pages.

* cited by examiner

*Primary Examiner* — Nicole M Ippolito
(74) *Attorney, Agent, or Firm* — Fitch, Even, Tabin & Flannery LLP

(57) ABSTRACT

A radiation treatment plan for a particular patient is optimized that provides corresponding resultant radiation dosing information. Such optimization can include, by one approach, calculating a corresponding influence matrix. Upon detecting at least one manual edit to at least one spot weight that corresponds to the radiation treatment plan, these teachings can provide for responsively generating new radiation dosing information in at least near real-time as a function of a corresponding influence matrix.

20 Claims, 5 Drawing Sheets

METHOD AND APPARATUS TO DETECT AND RESPOND TO RADIATION TREATMENT PLAN SPOT WEIGHT EDITS

TECHNICAL FIELD

These teachings relate generally to treating a patient's planning target volume with energy pursuant to an energy-based treatment plan and more particularly to responding to modifications of radiation dosing information.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called energy-based treatment plan often serves in the foregoing regards.

An energy-based treatment plan such as a radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Unfortunately, existing optimization techniques do not necessarily address all potential needs for all potential patients in all potential application settings. As one example in these regards, modulated proton scanning typically requires the optimization of so-called spot position and spot weights in order to obtain optimal dosing and dose rates. The automatic optimization of spot positions and weights, however, does not always produce satisfactory results.

It is possible to manually edit spot weights following optimization to improve anticipated results for a problematic region (or, alternatively, one can continue to use the optimization algorithm to add or change the optimization criteria in order to seek a better result). Prior art approaches in these regards, however, require recalculating the dose to thereby observe and assess the results of such modifications. Furthermore, such recalculations may be necessarily required multiple times in order to test/assess different possible adjustments to the plan. These approaches can require considerable time, sometimes requiring multiple hours. That expenditure of time can be at least inconvenient for both the patient and the technician(s)/physician(s), and as a result, a less than fully-suitable plan may be simply settled upon.

BRIEF DESCRIPTION OF THE DRAWINGS

The above needs are at least partially met through provision of the method and apparatus to detect and respond to radiation treatment plan spot weight edits described in the following detailed description, particularly when studied in conjunction with the drawings, wherein.

Figure 1:
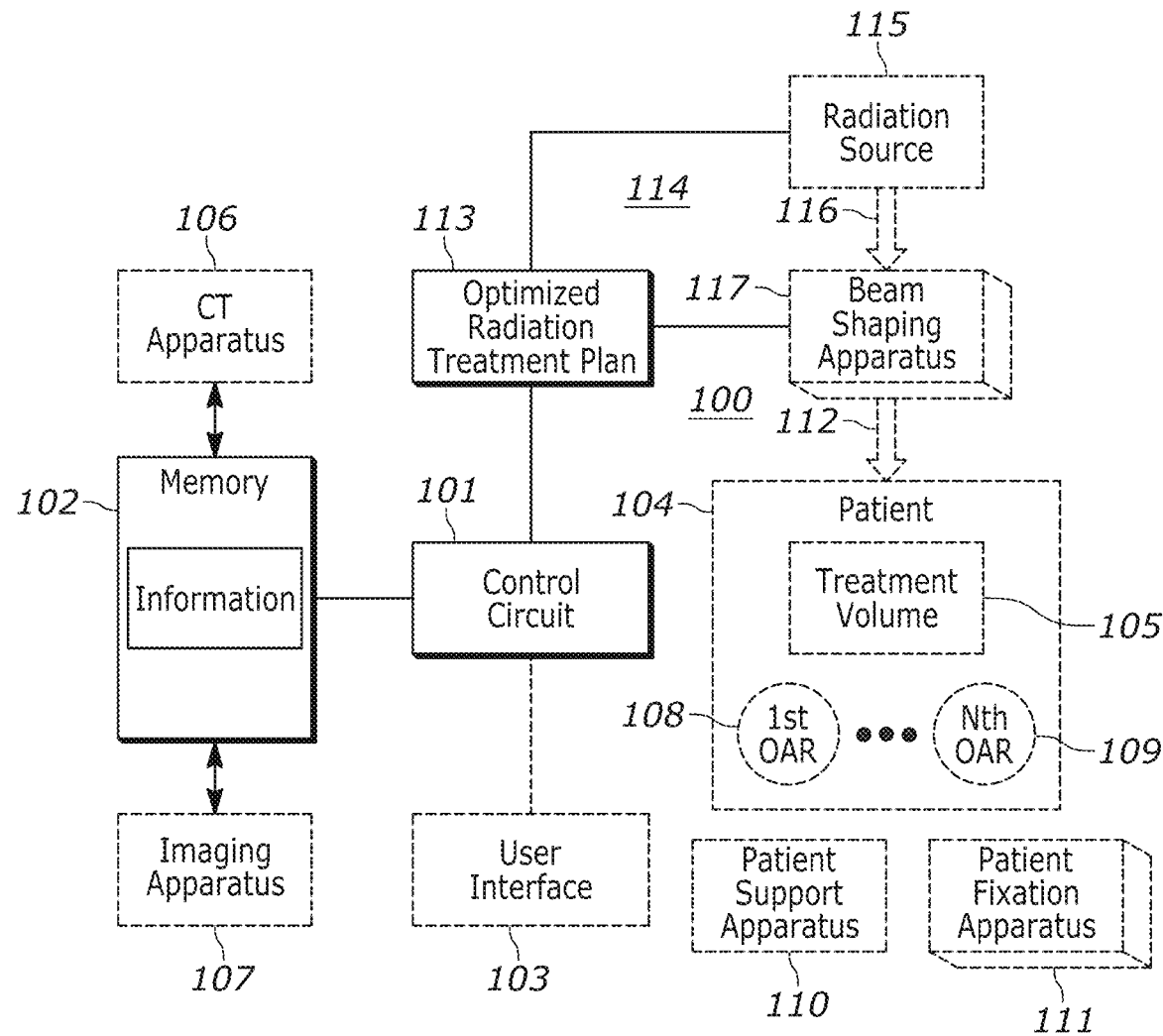
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate optimizing a patient treatment plan to administer therapeutic energy, such as a proton beam, to a particular patient.

By one approach, these teachings provide for optimizing a radiation treatment plan for a particular patient and providing corresponding resultant radiation dosing information. Such optimization can include, by one approach, calculating a corresponding influence matrix. Upon detecting at least one manual edit to at least one spot weight that corresponds to the radiation treatment plan, these teachings can provide for responsively generating new radiation dosing information in at least near real-time as a function of a corresponding influence matrix.

These teachings will accommodate various approaches to detecting such manual edits. By one approach, for example, a manual edit can be detected via a user interface when a user selects a region that includes a plurality of spots (using, for example, a cursor). By another approach, and as another example, a manual edit can be detected when a user selects individual spots.

By one approach, these teachings provide for generating the new radiation dosing information by multiplying the aforementioned influence matrix by the corresponding spot weights. The latter may comprise, for example, using vector multiplication.

These teachings are both flexible and practical in practice and will accommodate, for example, generating the new radiation dosing information by calculating a total radiation dose, calculating a dose rate, or both as desired.

These teaching accordingly support interactive dose modification in a treatment planning system. These teachings are highly flexible in terms of accommodating various approaches to how a user can interact with the treatment planning system. So configured, these teachings provide a simple and intuitive way to address problematic cases that the automatically optimized solution does not adequately address. Perhaps just as importantly, the corresponding results can be very quickly provided (for example, within 1 to 5 seconds as compared to, potentially, many hours required by many prior art approaches).

By permitting the user to see the results of their changes to spot weighting in at least near real-time, a given highly-effective radiation treatment plan can be more likely achieved in a practical application setting.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as radiation dosing information, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan 113 (such as, for example, an optimized radiation treatment plan). This energy-based treatment plan 113 typically comprises specified values for each of a variety of treatment-platform parameters during each of a plurality of sequential exposure fields. In this case the energy-based treatment plan 113 is generated through an optimization process. Various automated optimization processes specifically configured to generate such an energy-based treatment plan are known in the art. As the present teachings are not overly sensitive to any particular selections in these regards, further elaboration in these regards is not provided here except where particularly relevant to the details of this description.

By one approach the control circuit 101 can operably couple to an energy-based treatment platform 114 that is configured to deliver therapeutic energy 112 to a corresponding patient 104 in accordance with the optimized energy-based treatment plan 113. These teachings are generally applicable for use with any of a wide variety of energy-based treatment platforms/apparatuses.

In a typical application setting the energy-based treatment platform 114 will include an energy source 115 such as a source of ionizing radiation, a source of microwave energy, a source of heat energy, and so forth. For the sake of an illustrative example, it will be presumed here that the energy source 115 is a source of protons that provides a beam of protons to irradiate diseased tissue.

By one approach this energy source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the energy source 115 along that arcuate pathway, and may accordingly control when the energy source 115 starts moving, stops moving, accelerates, de-accelerates, and/or a velocity at which the energy source 115 travels along the arcuate pathway.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the energy source 115, and one or more energy-shaping apparatuses 117 (for example, beam-shaping apparatuses such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
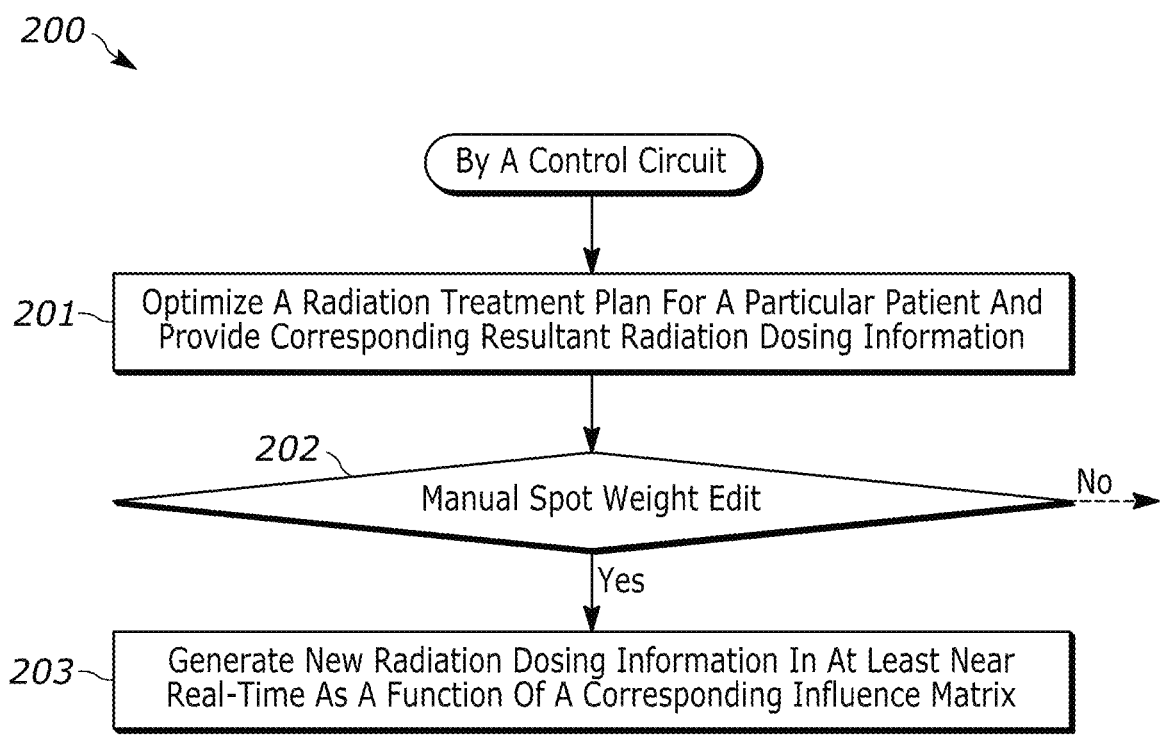
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described.

At block 201, this process 200 provides for optimizing a radiation treatment plan 113 for a particular patient 104 and providing corresponding resultant radiation dosing information. For the sake of an illustrative example, it will be presumed here that the radiation treatment plan 113 comprises a plan to administer scanning proton therapy.

Figure 8:
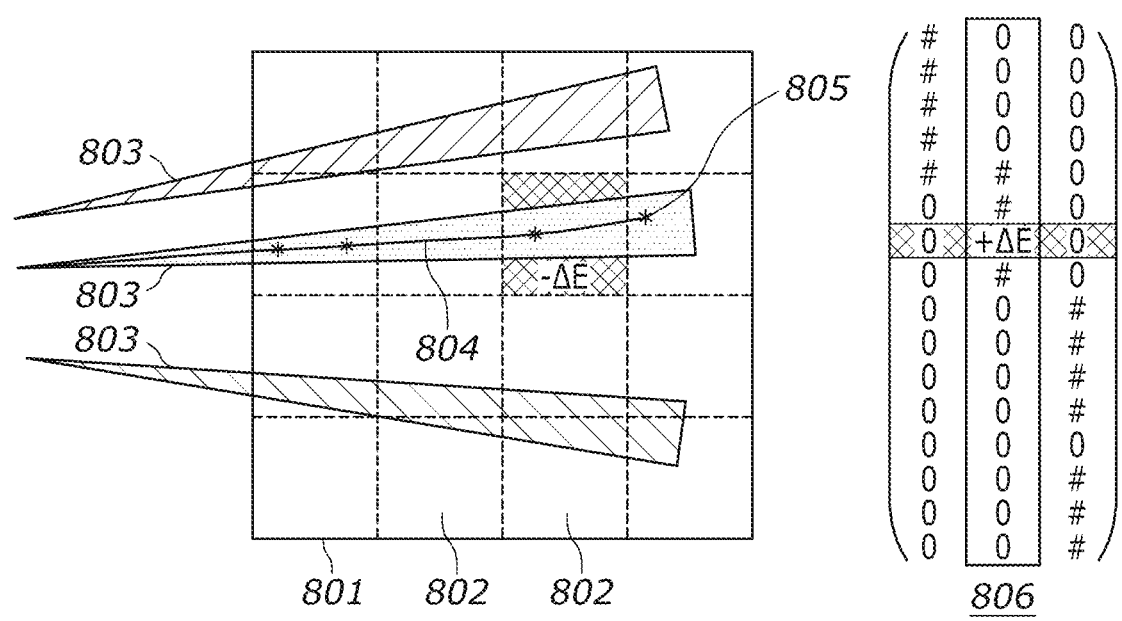
FIG. 8 comprises a schematic representation as configured in accordance with various embodiments of these teachings.

It will also be presumed here that optimizing the radiation treatment plan 113 includes calculating a corresponding influence matrix. Influence matrices are known in the art. An influence matrix specifies how each spot affects the dose (and hence specifies the contribution of each spot). For the sake of an illustrative example, and referring momentarily to FIG. 8, the depicted grid 801 corresponds to a two-dimensional patient comprising 4×4 voxels (two of which are denoted by reference 802). The wedges 803 are proton beams or "spots," and the broken line 804 is the trajectory of an individual proton inside the patient. The stars (one of which is denoted by reference 805) indicate collisions of the proton with particles in the medium where it loses and deposits some energy (where "dose" equals energy divided by local density).

Reference numeral 806 denotes the corresponding influence matrix. In this illustrative example the columns of the influence matrix each correspond to one spot and each row corresponds to one voxel. To form the influence matrix, the control circuit 101 simulates the trajectories of protons and adds all of their individual contributions to the influence matrix based on the spot the proton belongs to and the voxel where the dose is deposited.

Referring again to FIG. 2, at block 202 the control circuit 101 detects at least one manual edit to at least one spot weight that corresponds to the radiation treatment plan 113. (In the absence of detecting a trigger event, this process 200 can accommodate any of a variety of responses. Examples of responses can include temporal multitasking (pursuant to which the control circuit 101 conducts other tasks before returning to again monitor for a manual edit) as well as continually looping back to essentially continuously monitor for this trigger event. These teachings also accommodate supporting this detection activity via a real-time interrupt capability.)

Figure 3:
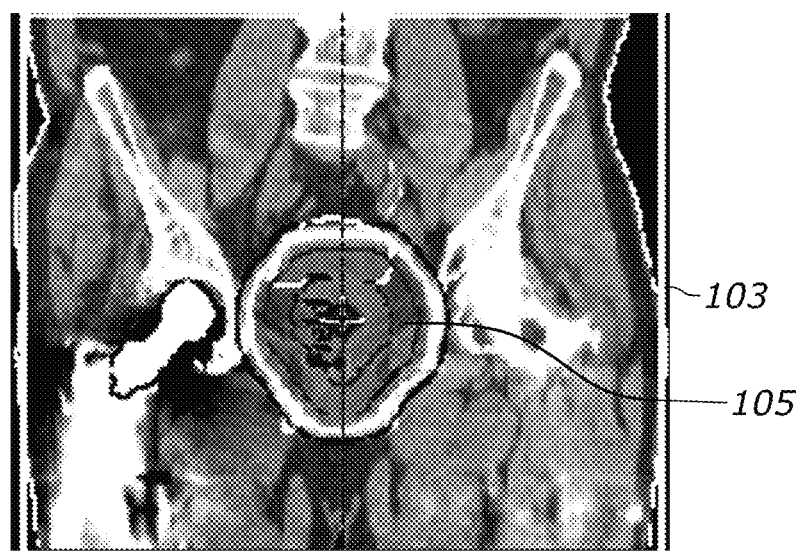
FIG. 3 comprises an illustrative screenshot as configured in accordance with various embodiments of these teachings.
Figure 4:
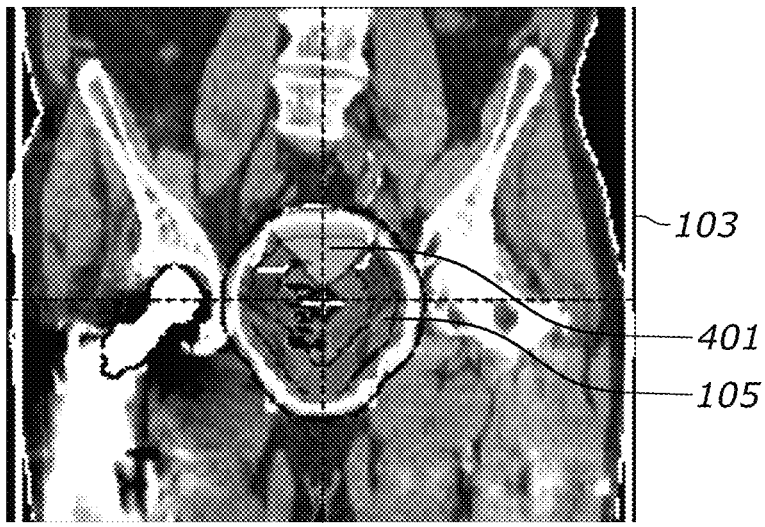
FIG. 4 comprises an illustrative screenshot as configured in accordance with various embodiments of these teachings.

These teachings will accommodate various approaches to detecting a manual edit. By one approach, and referring momentarily to FIGS. 3 and 4, FIG. 3 depicts the user interface 103 presenting a scanned image that includes scanned imagery of the patient's treatment volume 105 along with other patient features and dosing information. FIG. 4 depicts a region 401 of the treatment volume 105 that the user has selected (using, for example, a cursor control and selection device such as a mouse or a touch screen display). This region 401 corresponds to and includes a plurality of spots. By this approach, the control circuit 101 detects that selection activity as a manual edit.

Figure 6:
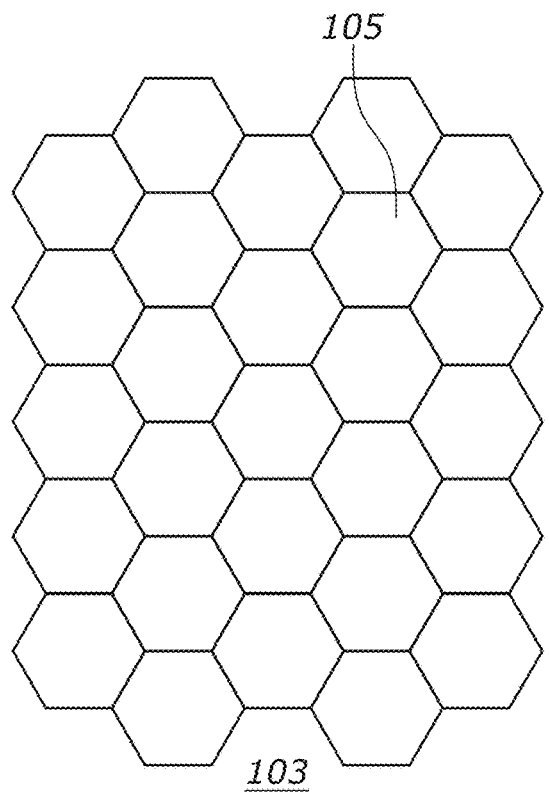
FIG. 6 comprises an illustrative screenshot as configured in accordance with various embodiments of these teachings.
Figure 7:
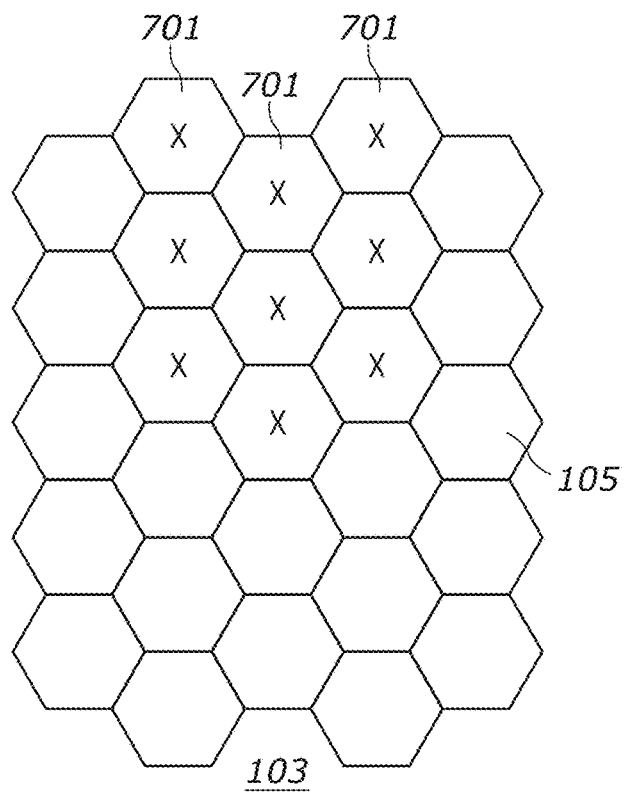
FIG. 7 comprises an illustrative screenshot as configured in accordance with various embodiments of these teachings.

By another approach, and referring momentarily to FIGS. 6 and 7, FIG. 6 depicts the user interface 103 presenting some individual spots that correspond to the treatment volume 105. FIG. 7 depicts, in turn, the user interface 103 presenting certain of the spots (generally denoted by reference 701) that correspond to individual spots that were selected by the user. In all of these cases the user can select a corresponding weight for the selected spots. These teachings will accommodate other approaches to detecting a manual edit as desired.

Upon detecting this event, at block 203 the control circuit 101 responsively generates new radiation dosing information in at least near real-time as a function of a corresponding influence matrix. (As used herein, the expression "near real-time" shall be understood to mean within two seconds. If desired, longer processing times can be accommodated. For example, the foregoing generation (and display) of the information may necessarily occur with, say, five seconds, ten seconds, twenty seconds, thirty seconds, one minute, and so forth as desired.) By one approach, to generate the new radiation dosing information the control circuit 101 calculates the dose by assigning the modified weight(s) (which may all be the same modified weight or different weights as desired) to the spots and multiplying the influence matrix with a vector of these spot weights. Calculating the dose this way is much faster than, for example, via simulating the dose deposition. These teachings will also facilitate determining how much each spot contributes to each voxel much faster than one would ordinarily find when using prior art approaches.

Figure 5:
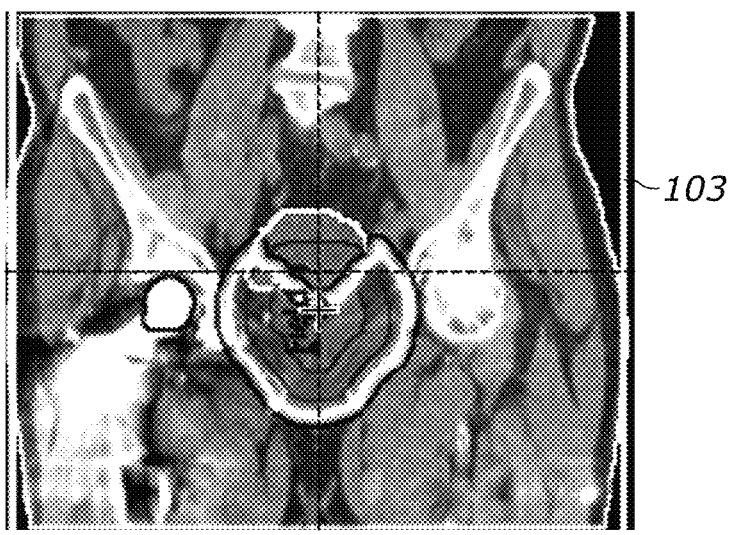
FIG. 5 comprises an illustrative screenshot as configured in accordance with various embodiments of these teachings.

The so-generated new radiation dosing information can comprise, for example, a calculated total radiation dose, a calculated dose rate, or both as desired. Referring to FIG. 5, the resultant calculated information can be presented graphically and/or alphanumerically by any means known in the art, such as but not limited to via the user interface 103. If desired, the speed of presentation of such information can be at least partially facilitated by use of a graphics processing unit. In another approach, in lieu of the foregoing or in combination therewith, the dose space can be parsed into distinct regions and only the presentation of the affected regions need be updated to reflect the modified dosing.

This use of the influence matrix makes it both simple and intuitive to modify spot weights to thereby change dose distribution while also accommodating a very fast calculation of and presentation of the corresponding results to the user.

Those skilled in the art will recognize that a wide variety of modifications, alterations, and combinations can be made with respect to the above-described embodiments without departing from the scope of the invention. Accordingly, such modifications, alterations, and combinations are to be viewed as being within the ambit of the inventive concept.

What is claimed is:

1. A method comprising:
   by a control circuit:
   optimizing a radiation treatment plan for a particular patient and providing corresponding resultant radiation dosing information;
   detecting at least one manual edit to at least one spot weight of the radiation treatment plan;
   in response to detecting the at least one manual edit, generating new radiation dosing information in at least near real-time as a function of a corresponding influence matrix.

2. The method of claim 1 wherein the radiation treatment plan comprises a plan to administer scanning proton therapy.

3. The method of claim 1 wherein the control circuit is configured to detect the at least one manual edit by detecting at least one of:
   selection of individual spots; and
   selection of a region that includes a plurality of spots.

4. The method of claim 1 wherein the control circuit is configured to detect the at least one manual edit by detecting user selections on a user interface.

5. The method of claim 1 wherein generating the new radiation dosing information as a function of the corresponding influence matrix comprises multiplying the influence matrix by spot weights.

6. The method of claim 5 wherein multiplying the influence matrix by spot weights includes using vector multiplication.

7. The method of claim 1 wherein generating the new radiation dosing information comprises calculating a total radiation dose.

8. The method of claim 1 wherein generating the new radiation dosing information comprises calculating a dose rate.

9. The method of claim 1 wherein generating the new radiation dosing information comprises calculating both a total radiation dose and a dose rate.

10. The method of claim 1 wherein optimizing the radiation treatment plan for the particular patient includes calculating the influence matrix.

11. An apparatus comprising:
    a control circuit configured to:
    optimize a radiation treatment plan for a particular patient and provide corresponding resultant radiation dosing information;
    detect at least one manual edit to at least one spot weight of the radiation treatment plan;
    in response to detecting the at least one manual edit, generate new radiation dosing information in at least near real-time as a function of a corresponding influence matrix.

12. The apparatus of claim 11 wherein the radiation treatment plan comprises a plan to administer scanning proton therapy.

13. The apparatus of claim 11 wherein the control circuit is configured to detect the at least one manual edit by detecting at least one of:
    selection of individual spots; and
    selection of a region that includes a plurality of spots.

14. The apparatus of claim 11 further comprising:
    a user interface that is operably coupled to the control circuit; and
    wherein the control circuit is configured to detect the at least one manual edit by detecting user selections on the user interface.

15. The apparatus of claim 11 wherein the control circuit is configured to generate the new radiation dosing information as a function of the corresponding influence matrix by multiplying the influence matrix by spot weights.

16. The apparatus of claim 15 wherein multiplying the influence matrix by spot weights includes using vector multiplication.

17. The apparatus of claim 11 wherein generating the new radiation dosing information comprises calculating a total radiation dose.

18. The apparatus of claim 11 wherein generating the new radiation dosing information comprises calculating a dose rate.

19. The apparatus of claim 11 wherein generating the new radiation dosing information comprises calculating both a total radiation dose and a dose rate.

20. The apparatus of claim 11 wherein optimizing the radiation treatment plan for the particular patient includes calculating the influence matrix.

* * * * *